United States Patent [19]

Harman et al.

[11] Patent Number: 5,288,634
[45] Date of Patent: Feb. 22, 1994

[54] METHOD OF INCREASING THE PERCENTAGE OF VIABLE DRIED SPORES OF A FUNGUS

[75] Inventors: Gary E. Harman; Xixuan Jin; Thomas E. Stasz, all of Geneva; George P. Peruzzotti, Webster; A. Carl Leopold, Ithaca; Alan G. Taylor, Geneva, all of N.Y.

[73] Assignee: Cornell Research Foundation, Inc., Ithaca, N.Y.

[21] Appl. No.: 975,998

[22] Filed: Nov. 13, 1992

Related U.S. Application Data

[63] Continuation of Ser. No. 841,270, Feb. 26, 1992, abandoned, which is a continuation of Ser. No. 562,285, Aug. 3, 1990, abandoned.

[51] Int. Cl.$^5$ .................... C12N 1/14; C12N 1/04; C12N 1/38
[52] U.S. Cl. ................. 435/254.1; 435/254.6; 435/260; 435/244
[58] Field of Search .............. 435/254, 260, 171, 243, 435/244, 254.1, 254.6

[56] References Cited

U.S. PATENT DOCUMENTS 4,837,155 6/1989 Tabachnik ..................... 435/254

OTHER PUBLICATIONS

Miller, Plant Physiology (Bethesda), 62(5), 1978, pp. 741–745.
Gindrat, Can. J. of Microbiol., 23, (5), 1977, pp. 607–616.
Harman et al., Phytopathology, 78(5), 1988 pp. 520–525.
ATCC Catalogue of Fungi/Yeasts, 17th edition, 1987, pp. 414–415.
Hoch, H. C., et al., Can. J. Bot. 51, 413–420 (1973).
Inch, J. M. M., et al., J. Gen. Microbiol. 133, 247–252 (1987).
Manandhar, J. B., et al., Phytopathology 63, 413–419 (1973).
Sung, J-M., et al., Phytopathology 71, 499–504 (1981).
Zuber, J., et al., Trans. Br. Mycol. Soc. 76, 433–440 (1981).
Cook, R. J., et al., Soil Sci. Soc. Am. Proc. 36, 78–82 (1972).
Cook, R. J., et al., Phytopathology 66, 193–197 (1976).
Cook, R. J., et al., Water Relations in the life-cycles of soilborne plant pathogens, In "Water Potential Relations in Soil Microbiology," Parr, J. F., et al., eds., pp. 119–139, 1981, Soil Sci. Soc. Am., Madison, Wis.

*Primary Examiner*—Douglas W. Robinson
*Assistant Examiner*—Susan M. Dadio

[57] ABSTRACT

This invention relates in part to the use of osmoticants to provide desiccation tolerance to growth producing cells of microorganisms upon drying and reconstitution.

This invention also relates in part to the discovery of liquid fermentation media permitting production of high levels of conidia of Trichoderma harzianum in liquid fermentation, and modifications to these media that produce conidia that are resistant to desiccation and that provide enhanced biocontrol efficacy.

10 Claims, 1 Drawing Sheet

METHOD OF INCREASING THE PERCENTAGE OF VIABLE DRIED SPORES OF A FUNGUS

This application is a continuation of application Ser. No. 07/841,270, filed Feb. 26, 1992, now abandoned, which is a continuation of Ser. No. 07/562,285, filed Aug. 3, 1990, now abandoned.

BACKGROUND OF THE INVENTION

It has been known for some time that cells, spores and the like, of microorganisms, which can be further propagated, tend to lose viability when dried, especially force dried e.g. by vacuum means. For commercial use of microorganisms, for example, as bioprotectants and herbicides and the like, dried material is the preferred item of commercial importance for both weight and handling considerations.

Trichoderma spp. are of increasing interest as bioprotectants against plant diseases (Harman and Lumsden, 1990, "The Rhizosphere" Lynch ed. pp.259–280, J. Wiley & Sons, NY; Harman et al., 1989, *Plant Dis.* 73:631–637; Papavizas, 1985, *Phytopathology* 74:1171–1175). Numerous papers have presented data on selection or production of strains for improved biocontrol efficacy (e.g. Hadar et al., 1984, *Phytopathology* 74:106–110; Sivan et al., 1987, *Plant Dis.* 71:587–592; Harman et al., 1989, supra; Stasz et al., 1988, *Mycologia* 80:141–150) and on delivery systems that provide effective biocontrol (Conway, 1986, *Plant Dis.* 70:835–839; Lewis et al., 1987, *Plant Pathol.* 36:438–446; Sivan et al., 1987, supra; Harman et al., 1989, supra). However, there is much less information on methods of producing large quantities of effective biomass as the active ingredient for microbial pesticides. Further, some work has relied upon semi-solid fermentation (Sivan et al., 1987, supra; Lewis et al., 1983, *Soil Biol. Biochem.* 15:351–357), which is of less interest to corporations wishing to market Trichoderma-based bioprotectants than is deep-tank fermentation.

Trichoderma spp. produces three kinds of propagules, i.e. hyphae, chlamydospores, and conidia (Papavizas, 1985, *Ann. Rev. Phytopathol.* 23:23–54). Biomass produced for biological control must retain a high level of viability after drying. Since hyphae do not withstand drying, hyphae biomass is not useful. Conidia are produced more abundantly than chlamydospores under optimal conditions; however, these optimal conditions usually include an aerial environment. Conidia are difficult to produce in submerged fermentation.

Some work published on production of Trichoderma biomass for biocontrol using liquid fermentation was directed toward production of chlamydospores, and required 10–21 days to produce optimal levels of biomass (Lewis et al., 1983, supra: Papavizas, et al., 1984, suora). Other work demonstrated that conidia could be produced rapidly under conditions of liquid fermentation, but did not investigate viability upon drying, or efficacy in biological control (Tabachaik, 1988, U.S. Pat. No. 4,837,155).

There are a number of requirements for biomass to be used for biological control, i.e. (1) biomass of appropriate spore composition must be produced in high levels rapidly, (2) the biomass must be able to withstand drying, (3) the dried material must have a high level of germinable, vigorous propagules, and (4) biomass should be of consistent quality from batch to batch.

This invention relates in part to the use of osmoticants to provide desiccation tolerance to growth producing cells of microorganisms upon drying and reconstitution.

This invention also relates in part to the discovery of liquid fermentation media permitting production of high levels of conidia of Trichoderma harzianum in liquid fermentation, and modifications to these media that produce conidia that are resistant to desiccation and that provide enhanced biocontrol efficacy.

BRIEF DESCRIPTION OF THE INVENTION

Figure 1:
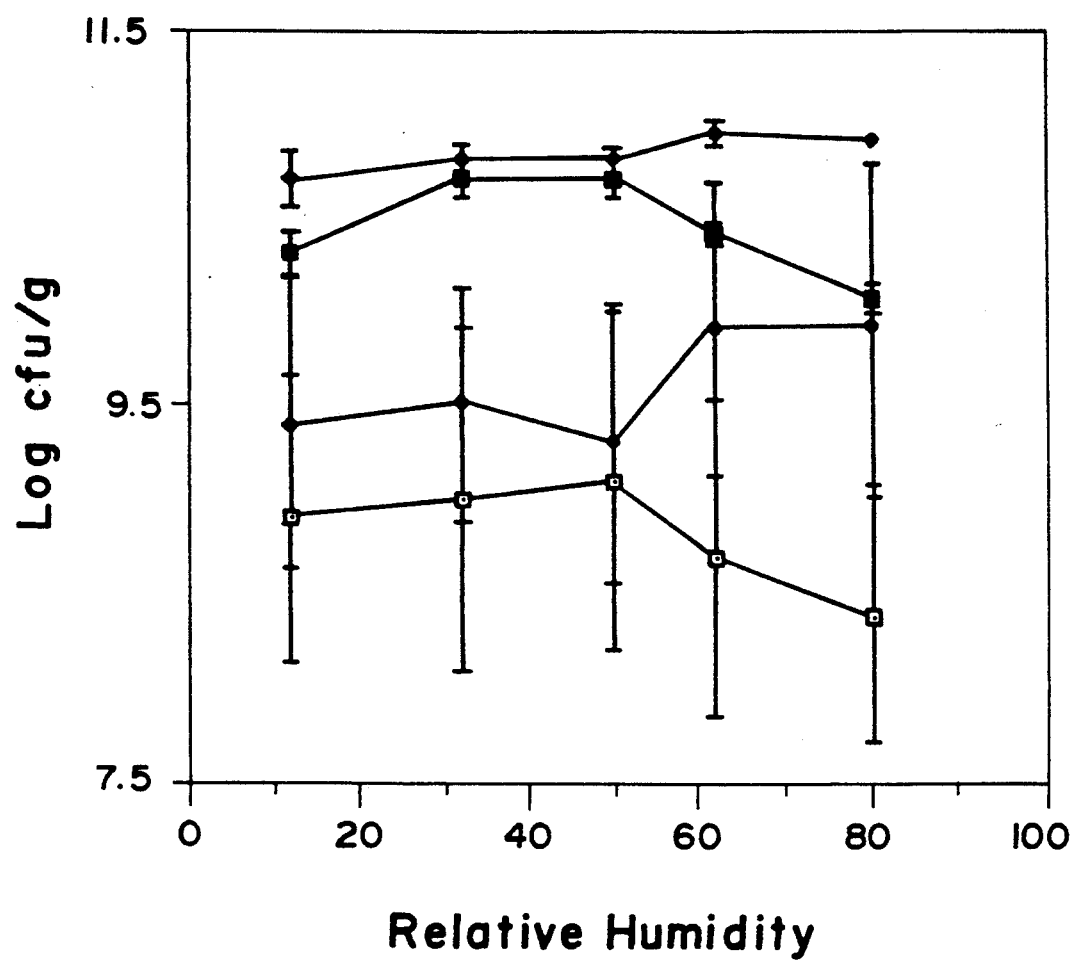
FIG. 1. graphs the log of cfu/g from conidial biomass equilibrated at different relative humidities for two weeks at 25° C. Biomass was produced in RM8+PEG and hydrated in 10% (w/v) sucrose (— —), produced in RM8+PEG and hydrated in water (— —), produced in RM8 and hydrated in 10% sucrose (— —), or produced in RM8 and hydrated in water (— —).

This invention relates to a method of enhancing the desiccation tolerance of cells of fungi or bacteria capable of reproducing the fungi or bacteria so that, once vacuum dried, they can be reconstituted with a higher proportion of viable cells. The method of the invention has applicability to virtually any microorganism cells which, when vacuum dried, tends to have reduced viability when reconstituted or resuspended in water or other aqueous medium. The method of the invention is particularly applicable to cells of Trichoderma, Gliocladium, Colletotrichum, Fusarium spp. and Pseudomonas. The presently preferred species is Trichoderma and the description which follows is largely directed to the production of viable Trichoderma conidia. However, the method of the invention can be adapted to virtually any aqueous medium based reproduction process.

This invention also relates to a method for enhanced production of Trichoderma conidia.

The invention in one aspect comprises adding to the microorganism production medium, at some point prior to harvesting and drying cells, an osmoticant adapted to protect the cells of the microorganism when subjected to drying by vacuum or other means including air drying.

Typically, microorganisms are grown in an aqueous medium adapted to support desired growth. The medium contains, depending on the microorganism, required growth supporting constituents such as nitrogen sources, carbon sources, buffers, essential minerals, vitamins, antibiotics and the like. Likewise, the growth conditions including shaking or stirring, light requirements, aeration, buffering and the like vary from microorganism to microorganism. Those skilled in the art are well aware of the growth medium requirement and growth conditions for particular microorganisms, and it is not necessary therefore to set forth examples in detail. For Trichoderma, for example, see U.S. Pat. No. 4,837,155 to Tabachaik.

As employed herein, osmoticant refers to a material which when added to the growth medium decreases osmotic potential (i.e. lessens water availability to the microorganism).

The osmoticant employed in the method of the invention can be virtually any osmoticant which, in the amounts employed, is nontoxic and nongrowth-inhibitory to the particular microorganism being produced, and which when employed provides an osmotic potential of between about $-1.5$ and about $-2.1$ mPa (megaPascals). Examples of such materials include carbohydrates such as mannitol, salts such as $MgCl_2$, polyalkylene oxides such as polyethylene glycol.

The osmoticant can be added to the growth medium in the desired osmotic potential creating amounts at any time prior to collecting and drying microorganisms cells or spores. For example, the osmoticant can be added to the growth medium prior to inoculation with a starter culture. Most preferably, the osmoticant is added to the aqueous growth medium after inoculation, but before the growth phase is substantially complete, i.e. after growth has been established and while the growth phase is active.

DESCRIPTION OF PREFERRED EMBODIMENTS

Generally, a preferred method of the invention directed toward increased Trichoderma conidia production comprises placing an inoculant comprising Trichoderma spores in a sufficient volume of a suitable liquid medium to permit production of Trichoderma conidia. The inoculated medium is maintained under substantially constant illumination agitation and aeration at a temperature from about 25° C. to about 30° C. The pH of the medium is maintained throughout from about 5.8 to about 7.0. The culture is maintained for a sufficient time, until the density of the conidia produced from the inoculant is about $1\times10^8$ conidia per ml. The conidia are then harvested.

The most preferred medium employed in the preferred method of the invention is a minimal media which promotes Trichoderma conidial growth, i.e. a medium containing no vitamins and the like, but which contains a nitrogen source e.g. $KNO_3$, a carbon source e.g. a sugar such as sucrose, a buffer, preferably $K_2HPO_4$ or $KH_2PO_4$, magnesium e.g. $MgSO_4$; and iron e.g. $FeCl_3$.

More broadly, alternative media can comprise a carbon source, a nitrogen source, $MgSO_4$, $FeCl_2$, $MnSO_4$, KCl and $K_2HPO_4$. It can also contain vitamins and antibiotics. The pH may be maintained by means of a buffer.

The carbon source can be a combination of potato dextrose broth, with other carbon compounds such as glucose, sucrose, maltose, fructose, cellulose starch, laminarin, malt extract or mixtures thereof. The nitrogen source can also be ammonium nitrate.

The method can be practiced as, for example, set forth in the Examples, which follow or alternatively in the following manner:

The inoculant containing medium is maintained under substantially constant illumination agitation and aeration at a temperature from about 25° C. to about 30° C. and at a pH from about 5.8 to about 7.0 for a sufficient period of time until the density of conidia produced from the inoculant is at least $1\times10^8$ conidia per ml. Once the desired density has been reached, the Trichoderma conidia so produced are harvested. The osmoticant is added at the point the growth is underway i.e. when the density of conidia begin to increase.

As described in U.S. Pat. No. 4,837,155, a medium that is suitable for the large scale culture of Trichoderma spp. conidia is a liquid basal medium that contains potato dextrose broth as a carbon source. The medium also contains an additional carbon source and a nitrogen source.

The carbon source of the medium is a combination of potato dextrose broth with another carbon source selected from the group consisting of glucose, sucrose, maltose, fructose, cellulose, starch and laminarin. The medium may also optionally contain malt extract.

This carbon enriched medium should contain from about 1 to about 4 grams per liter of potato dextrose broth and preferably from about 2 to about 3 grams per liter. It should contain from about 5 to about 15 grams per liter of glucose or its alternative e.g. sucrose, maltose, fructose, cellulose, starch, laminarin or some other suitable carbon source. Mixtures of these carbon sources can also be used. The concentration of malt extract should be from about 5 to about 15 grams per liter and is preferably from about 8 to about 12 grams per liter. The malt extract is believed to give the conidia more vigor and vitality.

A variety of nitrogen sources can be used, preferably nitrates or nitrites. Ammonium nitrate has been found to be quite suitable.

The medium also contains suitable amounts of minerals and trace elements such as $MgSO_4$, $FeCl_2$, $MnSO_4$, and $ZnSO_4$. Hydrates of these compounds can also be used, e.g. $MgSO_4$—$7H_2O$, $FeCl_2$—$H_2O$, $ZnSO_4$—$7H_2O$. The medium also contains suitable amounts of KCl, and $K_2HPO_4$. Other trace elements and minerals may also be added.

The medium can contain a vitamin. Thiamine-HCl was found to be suitable as a vitamin, but other vitamins may also be used. The medium may also contain antibacterial compounds such as the antibiotics chloramphenicol, ampicillin, streptomycin or penicillin. Chloramphenicol is the preferred antibacterial compound.

In a preferred embodiment of U.S. Pat. No. 4,837,155, the liquid medium comprises per liter of distilled water, $MgSO_4$—$7H_2O$, 0.2 g; KCl, 0.2 g; $K_2HPO_4$, 3.99 g; $KH_2PO_4$, 1.99 g; $FeCl_2$—$4H_2O$ 0.002 g; $MnSO_4$—$H_2O$, 0.002 g; $ZnSO_4$—$7H_2O$, 0.002 g; thiamine-HCl, 0.001 g; chloramphenicol, 0.25 g; potato dextrose broth, 2.4 g, glucose, 10.0 g; malt extract, 10.0 g; and $NH_4NO_3$, 1.0 g.

The pH of the culture medium is preferably maintained within a pH range of 5.8 g to 7.0, throughout the fermentation process by use of a buffer system. The buffer system used is preferably a phosphate buffer system. In a specific embodiment of this invention, the phosphate buffer system used is a mixture of $KH_2PO_4$—$K_2HPO_4$. A Tris-buffer system can also be used.

The inoculant-containing medium can be maintained under constant illumination by using any light source, e.g. incandescent and fluorescent lights can be used. Sunlight can also be used if the reactor vessel containing the medium is sufficiently transparent. The aeration rate for a 50–400 liter volume of culture medium is usually within the range of 0.1–10 vvm.

At the end of the fermentation period, the conidia in the presence of the osmoticant in the medium are harvested. A common way of separating the conidia from the medium is by filtration or centrifugation. After separation, the conidia are dried by vacuum or other suitable means.

By using the methods of this invention it is possible to grow large quantities of Trichoderma spp. conidia. The Trichoderma spp. can be any species of Trichoderma such as *T. harzianum*, *T. hamatum* or *T. viride*. For example, *T. harzianum* can be grown within 36 to 60 hours to yields of $5\times10^4$ to $10^9$ conidia per ml in 500 liter reactors. The Trichoderma spp. conidia grown in large quantities according to this invention can be used as the active ingredient in fungicidal compositions.

These fungicidal compositions are useful in protecting commercial plants from soil-borne pathogenic fungi.

With particularity as to the aspect of the invention related to the enhanced production of Trichoderma conidia, the media consists essentially of a minimal medium which promotes Trichoderma conidial production, i.e. a medium containing no vitamins and the like, but which contains a nitrogen source e.g. a sugar such as sucrose, a source of K & P which, if properly selected, can also serve as a buffer preferably $K_2HPO_4$ or $KH_2PO_4$, magnesium e.g. $MgSO_4$ and iron e.g. $FeCl_3$; for example, Czapek Dox broth which contains per liter 30 g sucrose, 3 g $KNO_3$, 1 g $K_2HPO_4$, 0.5 g $MgSO_4$, 0.5 KCl and 0.1 g $FeSO_4$ or a modified Richard's medium as described in the Examples.

The growth media is inoculated and the growth conducted in a manner described above and the conidia harvested.

In the most preferred conidial growth method, the minimal media is augmented with conidial growth stimulating amount of a vegetable juice e.g. tomato juice or V8 vegetable juice to provide enhanced production of Trichoderma conidia.

EXAMPLES

Materials and Methods

Organism and Growth Conditions

Strain 1295-22 (ATCC 20847) of *T. harzianum* Rifai was used in all experiments. This strain was prepared by protoplast fusion (Stasz et al., 1988, suora), and is a highly effective biocontrol agent (Harman et al., 1989, supra).

Inoculum was obtained by growing the fungus on Bacto Potato Dextrose Agar until a densely sporulating colony covered the entire agar surface. Spores were removed by scraping with a spatula. Spores so obtained were placed in 15% (v/v) aqueous glycerol, divided into 1 ml aliquots, placed in sterile microcentrifuge tubes, and stored at −20° C. until use.

All cultures were grown in 250 ml Erlenmeyer flasks containing 100 ml medium. Each flask was innoculated with 1 ml of a 10-fold dilution of the glycerol-spore suspension that contained $2\times10^8$ conidia/ml. Cultures were grown with shaking at 150 revolutions per minute at 25±2° C. for 4 days. Preliminary experiments indicated that this was the minimum time required for maximal conidial production.

Harvesting and Drying of Cultures

Cultures were combined prior to harvest, and were homogenized using a Tekmar tissue homogenizer (Thomas Scientific, Philadelphia, Pa.) at full speed for 3 minutes. Homogenates were centrifuged at 8000×g for 10 minutes, and the supernate was discarded. The pellet was suspended in distilled water at one half the original volume of medium, and the mixture was again centrifuged and the supernate discarded. The pellet was then removed from the centrifuge tube with a spatula, spread in a thin layer in a petri dish and then dried either in the air stream in a transfer hood or placed in a vacuum drier overnight, as indicated.

Media

Media considered in this work were of several classes. These were minimal media, a complete defined medium minimal media amended with V-8 juices, and complex undefined media. Representatives of the first class were Czapek Dox broth (Difco Laboratories, Detroit, Mich.), a modification of Richard's medium (Hawksworth et al, 1983, "Ainsworth and Bisby's Dictionary of the Fungi 7th Ed.", Commonwealth Mycol Inst. Kew, Slurry, U.K.) that contained, in units/1, 10g $KNO_3$5 g $KH_2PO_4$, 1.3 g anhydrous $MgSO_4$, 8 g sucrose, and 20 mg $FeCl_3$. The complete defined medium was Neurospora minimal medium (Beadle, 1945, *Physiological Rev.* 25:643–663), and the complex, undefined media were potato dextrose broth (Difco Laboratories, Detroit, Mich.), trypticase soy broth (BBL Microbiology Systems, Cockeysville, N. Dak.). In some experiments, Czapek Dox broth and the Richard's medium were modified by the addition of 150 ml of V8 vegetable juice (Campbell Soup Co., Camden, N.J.) to each 1 of medium; the resulting media are designated CD8 and RM8, respectively. All media were adjusted to a pH of 6 before use. In some cases osmotic potential of media was determined by freezing point depression using a Micro Osmette (Precision Systems, Inc. Natick, Mass.).

Assays

Total numbers of propagules and colony forming units (cfus) were determined in the mixtures from cultures just after homogenization and in drying preparations. Propagule numbers were determined by direct counts in a Petroff-Hausser chamber (Thomas Scientific, Philadelphia, PA). Cfus were determined by plating serial dilutions of various spore preparations onto potato dextrose agar amended with Igepal Co-630 (Applied Science Labs, Deerfield, Ill.) to limit colony diameter (Norton and Harman, 1985, *Can. J. Bot.* 63:1040–1045). Prior to enumeration or plating, dry spore samples were soaked in sterile distilled water, unless other noted, for 2 hours, and then homogenized in a Tekmar tissue homogenizer at full speed for 3 minutes.

Test of biocontrol efficacy were conducted by planting treated seeds in soil infested with *Pythium ultimum* Trow. Two seed treatment methods were employed, i.e. a slurry treatment for snap beans and a procedure designated as double coating for cucumbers (Taylor et al., U.S. patent application Ser. No. 07/446,497, filed Dec. 4, 1989, hereby incorporated reference). Ten g of cucumber (Cucumis sativus L. "Poinsett 76") seeds were first treated by spraying 31 mg of Trichoderma spore suspensions contained in 1 ml of 10% (w/v) aqueous Pelgel (Nitragin Corp., Milwaukee, Wis.; Pelgel is an adhesive) onto seeds in a rotating drum. This treatment was overlain with a second layer that consisted of 2 g of Leonardite shale (Agro-Lig, American Colloids Co., Skokie, Ill.) in an adhesive suspension consisting of 5% (w/v) Polyox N-10 (Union Carbide Corp., Danbury, Conn.), again by spray application in a rotating drum.

Snap bean seeds (Phaesolus vulgaris cv. 'Bush Blue Lake 47') were treated using a slurry treatment. In this treatment, 100 g of seeds were treated by spray application of 310 mg of Trichoderma spore preparations contained in 6 ml 5% Polyox N-10 suspension in a rotating drum.

Sugars were analyzed in samples by first freezing preparations in liquid nitrogen and grinding. They were then hydrated in deionized water and filtered before lyophilization. Samples are then deriviatized and injected onto an Alltech SE-45 capillary column.

Results

Effect of culture medium

The various media differed markedly in their ability to support conidial production (Table 1). Complex undefined media (i.e. potato dextrose broth, malt extract broth, and trypticase soy broth) or the complete defined media (Neurospora minimal broth) produced relatively few conidia, and after drying, the cfu/g levels of these media was only $10^{6.7}$–$10^{7.8}$ (Table 1).

were each useful osmoticants. In preliminary experiments, we also investigated the influence of the time of addition of these materials. As a consequence, 50 ml of 60% (w/v) PEG in sterile water was added to 50 ml of cultures grown for 24 hours in RM8. Mannitol and $MgCl_2 \cdot 7H_2O$ were added at the rate of 7.4 and 2.7 g, respectively, per 100 ml MR8 at the time of medium preparation. Quantities of osmoticant were calculated to give approximate equal osmotic potentials; values for RM8, RM8+annitol, and RM8+$MgCl_2$ were measured

TABLE 1

Comparison of the ability of various media to support growth and conidiation[a] of *Trichoderma harzianum* strain 1295-22, and of the ability of dried propagules to germinate.

| Medium | Yield/ 100 ml Medium (mg) | Log Propagules/g Dry Weight | Percent Conidia in Culture | Percent Conidia/g Dry Weight | Log Cfu/g Dry Weight | Germination Percent[b] |
|---|---|---|---|---|---|---|
| Potato dextrose broth | 228 C | 8.8 B | 20 B | 46 D | 7.2 CDE | 2.7 A |
| Malt extract broth | 123 CD | 8.8 B | 39 B | 59 CD | 7.2 DE | 3.4 A |
| Tripticase soy broth | 352 B | 8.5 B | 38 B | 74 BC | 6.7 E | 1.9 A |
| Modified Richard's broth | 49 D | 11.1 A | 91 A | 97 A | 9.5 A | 2.2 A |
| RM8 | 434 AB | 11.1 A | 97 A | 95 A | 9.5 A | 2.3 A |
| Czapek Dox broth | 31 D | 10.7 A | 92 A | 91 A | 8.3 BC | 1.6 A |
| CD8 | 479 A | 10.8 A | 90 A | 91 A | 9.0 AB | 1.7 A |
| Neurospora minimal broth | 131 CD | 9.6 B | 71 A | 87 AB | 7.8 CD | 5.9 A |

[a]Numbers followed by dissimilar letters within columns are significantly different according to Waller and Duncan's test (GLM procedure, SAS Institute, Cary, NC). Values given are means averaged over two separate replicates.
[b]Germination percent was calculated as the ratio of cfu/g divided by the propagules/g.

These levels are quite low, since one g of this fungus contains about $1-2 \times 10^{11}$ conidia. Minimal media (modified Richard's and Czapek Dox) were much more effective than more complex media; dried biomass from these media were >90% conidia. Consequently, both propagules/g and cfu/g were 10-100 fold higher from these minimal media than from more complex ones. However, yields from minimal media were 2-3 times lower than from more complex media. Therefore, additives to minimal media that increased yield while still giving rise to a high percentage of conidia in the biomass were sought. Addition of V8 juice to minimal media increased yields 7-10 fold, while biomass remained primarily conidial (Table 1). RM8 and CD8 appeared to give similar and superior results to the media, and RM8 was used in all subsequent experiments.

Germination of Propagules

Even though relatively high yields of conidia were produced in RM8 and CD8, the ability of these conidia to germinate after drying was low. The rate and extent of drying was important; drying of biomass in vacuum, which could be accomplished overnight, gave 1-11% germinable propagules, while slower drying in ambient air, which took up to 60 hours, resulted in as many as 30% germinable conidia. However, drying of large volumes of biomass in an air stream is not commercially practical. Additions to media that gave rise to conidia resistant to rapid drying were sought.

Media of Low Osmotic Potential

The use of various additives to RM8 to decrease osmotic potential (i.e. to make water availability less) was investigated, and in preliminary experiments determined that polyethylene glycol 8000 (PEG) (Sigma Chemical Co., St. Louis, Mo.), $MgCl_2$ and mannitol using freezing point depression, and were $-0.82$, $-1.91$, and $-1.76$ mPa, respectively. The presence of PEG interfered with accurate measurement of the freezing point, and the osmotic potential for RM8+PEG was calculated to be $-2.10$ using the equations of Steuter et al., (1981, *Plant Physiol.* 67:64-67).

All three osmotic media gave rise to conidial biomass that was much more resistant to drying than that produced in MR8 (Table 2). The cfu/g of dried biomass increased about 10-fold in spores produced in media of low osmotic potential as compared to those produced in RM8 (Table 2), while biomass yields were not affected (data not shown).

TABLE 2

The effect of osmoticant additions to Richard's medium plus V8 juice on germinability of conidia after drying[a].

| Medium | Log Propagules/g | Log Cfu/g | Germination Percent |
|---|---|---|---|
| RM8 | 11.0 B | 10.0 B | 12% C |
| RM8 + PEG | 11.1 B | 11.0 A | 71% A |
| RM8 + $MgCl_2$ | 11.3 A | 11.1 A | 53% B |
| RM8 + Mannitol | 11.0 B | 10.8 A | 60% AB |

[a]Numbers within columns followed by dissimilar letters are significantly different according to Waller and Duncan's test (GLM procedure, SAS Institute Inc., Cary, NC) Means are average over several replicates; the values for RM8 are averages over four replicates, for RM8 + PEG over three replicates, and for RM8 + $MgCl_2$ and mannitol, over two replicates.

Effect of Relative Humidity and Osmotic Potential on Conidial Germination

Anecdotal observations indicated that spore moisture level had an effect upon germination of conidia grown in media of low moisture content. Such effects might reflect damage due to rapid influx of water into very dry spores, an effect that might be ameliorated by hydration of spores in a solution of low osmotic potential.

Therefore, spores produced in RM8 or RM8+PEG were incubated for two weeks in relative humidities of 12, 32, 50, 68, and 80% at 25° C. These humidities were maintained in sealed desiccators over various saturated salt solutions (Winston and Bates, 1960, Ecology 41:232-237). Spores were than hydrated either in water or in 10% sucrose, and then transferred to potato dextrose agar plus Igepal to determine the number of viable cfu. This level of sucrose is sufficient to stabilize protoplasts of Trichoderma (Stasz et al., 1988, supra) and so should prevent spore damage by rapid water influx into hydrating conidia.

Conidia produced in RM8 gave rise to fewer cfu/g than those produced in RM8 +PEG (FIG. 1). When all values with spores grown in RM8 were combined and compared with those grown in MR8 +PEG, a T test revealed the difference to be highly significant (P=>0.01). With either RM8 and RM8+PEG, suspension of spores in sucrose rather than water resulted in greater cfu recovery (FIG. 1, P=>0.01). Standard deviations for determinations with MR8 were much larger than with MR8+PEG. Given the same production and suspension medium there was little difference in the number of cfu produced from spores equilibrated at different relative humidities, regardless of the medium in which they were produced (FIG. 1). In the case of spores produced in RM8+PEG, an F test indicated that this trend was significant (P=0.05).

Ability of Spore Preparations to Protect Seeds

The ability of spores produced in an industrial fermenter, in a medium similar to MR8 (hereinafter referred to as fermenter biomass) or RM8+PEG produced in shaker flasks to protect seeds were compared on two crops. With cucumber seeds, spores produced in RM8+PEG were more effective in protecting seeds against Pythium ultimum than those in the fermenter biomass. This may be at least partially due to the fact that, with MR8+PEG, cfu levels tended to be somewhat higher than when seeds were treated with the same amount of fermenter biomass (Table 3), although this difference was not significant. With bean seeds, both preparations were capable of a high level of protection, and cfu levels were similar (Table 3).

TABLE 3

Effect of seed treatment[a] with different preparations of Trichoderma harzianum on stands[b] of bean and cucumber seeds planted in soil infested with Trichoderma harzianum.

| Seed Treatment | Cucumber Stand(%) | Cucumber Log Cfu | Bean Stand(%) | Bean Log Cfu |
|---|---|---|---|---|
| None | 20C | — | 40B | — |
| Slurry or coating without T. harzianum | 2D | — | 20B | — |
| Slurry or coating with fermenter biomass | 43B | 3.95 | 86A | 4.80 |
| Slurry or coating with MR8 + PEG | 64A | 4.22 | 92A | 4.78 |

[a]Bean seeds were treated with a slurry treatment, while cucumbers were treated with a seed coating.
[b]Means were averaged over two replicates, numbers within columns followed by dissimilar letters are significantly different according to Waller and Duncan's test (GLM procedure, SAS Institute, Cary, NC).

Sugar Profiles of Spore Preparations

The sugar components of fungal spores may affect the ability of spores to survive desiccation. Therefore, we determined the profiles of these compounds in spore preparations produced in RM8 or RM8+PEG. sorbitol was the predominant sugar in spores, but its concentration was unaffected by the medium used for spore production (Table 4). Fructose, $\alpha$-glucose, $\beta$-glucose, and galactose were present at lower concentrations, and were unaffected by medium. Conversely, trehalose was not detected in spores produced in RM8, but increased to about 8% of the total sugar in spores produced in RM8+PEG>

TABLE 4

Composition of endogenous sugars and percent viable spores of two lots of T. harzianum biomass produced in different media[a].

| Sugar | MR8 | MR8 + PEG |
|---|---|---|
| Quality of sugars ($\mu$g/g) after growth in | | |
| Fructose | 2.1 | 1.8 |
| $\alpha$-Glucose | 3.2 | 5.0 |
| $\beta$-Glucose | 3.4 | 7.2 |
| Galactose | 2.3 | 4.5 |
| Sorbitol | 475 | 450 |
| Trehalose | none detected | 41[b] |
| Percent Germinable Spores | | |
| | 7 | 73[b] |

[a]Data presented are mean values obtained from two experiments employing separate lots of spores.
[b]Numbers are significantly greater than those obtained with spores produced in MR8 according to an T test at the 0.09 level (trehalose) and the 0.007 level (percent germinable spores).

Discussion

It is highly preferred that biomass produced for use in biological control must have a number of properties if it is to have maximum commercial advantage. First, it should be possible to produce appropriate microbial structures economically in liquid fermentation media. Second, the biomass thus prepared should be preserved against microbial contamination; this usually requires drying or formulation into a medium with low levels of water availability (Kenney et al, 1981, "Beltsville Symposium Agri Res. 5 Biolog, Control in Crop Production" Papavizas ed. pp. 143-150, Allenheld, OS Min Pub. London). Third, biomass should be effective at economically reasonable rates. This criterion requires that as many of the propagules as possible be germinable and effective. Fourth, the biomass or formulations prepared from it should be effective over the range of environmental conditions under which it may be employed. Finally, preparations should have as long a shelf life as possible. It is difficult for any living organism to tally meet all of these criteria, but biocontrol preparations should meet as many of these as possible.

Products prepared by the method of the invention met many of these criteria. Media composed of inexpensive ingredients were developed that give good yields of conidia of T. harzianum. The invention focused on conidia rather than chlamydospores because, under optimal conditions for either, conidia usually are produced much more abundantly than are chlamydospores. In submerged culture, Lewis et al., (1983, supra), produced at most about $1 \times 10^9$ chlamydospores/g of dry preparation, which is less than the conidial levels produced in this study. Further, chlamydospores are embedded in hyphae, while conidia are released from philades as single cells into the medium. Therefore, it may be easier to prepare uniform powders or other formulations from conidial preparations than from those in which chlamydospores are the primary useful structure.

The conidial biomass produced in RM8 r CD8 was, however, suboptimal. Only 1-10% of the conidia were viable following drying, so any microbial pesticide could have only 1–10% active ingredient. Not only would this require a greater (and therefore less economical) dosage to accomplish the expected result, but nonviable propagules may actually be detrimental to biocontrol. Nutrients may stimulate plant pathogenic fungi or microorganisms that are strongly competitive with the bioprotectant, and therefore lessen effectiveness of the biocontrol agent (Harman, 1990, "New Directions in Biological Control: Alternative for Suppressing Agricultural Pests and Diseases" Baker et al., ed. pp. 779–792 A.R. Liss Inc., N.Y.); such nutrients could arise from dead propagules of the biocontrol agent. In addition, the reproductability in numbers of cfu/g was poor in spores produced in RM8, which will make production of reliable and consistent bioprotectant preparations difficult.

These shortcomings largely were overcome by producing conidia in the presence of various osmoticants. Spores so produced withstood harvesting and drying much better than those produced in RM8, and had consistently high levels of cfu/g.

In hindsight, it is rational that spores produced under conditions of low osmotic conditions should provide conditions for adaptation of the organism to dehydration or the water stress. Such effects have been noted in yeast and in Euglena (Rapoport et al., 1984, *mikrobiologiya* 52:556–559; Dwyer, 1986, *Plant Cell Environ.* 9:485–489). In a variety of organisms, including yeast and nematodes, such adaptation includes the synthesis of increased quantities of trehalose (Rapoport et al., 1984, suora; Crowe and Crowe, 1986, "Membranes, Metabolism and Droy Organisms": Leopold ed., pp. 210–230, Comstock Publishing, Ithaca, N.Y.). Trehalose synthesis appears to be a common response to stress (panek et al., 1986, ibid pp. 123–142). Increased trehalose contents have been associated with improved yeast quality, including it gassing and baking abilities (Pollock et al., 1951, *Cereal Chem.* 28:498–505), properties which should be associated with its ability to grow and to proliferate rapidly. Trehalose and other nonreducing polyols stabilize membranes at low water availability levels, and this effect probably is at least partially responsible for the increased stability of Trichoderma spores that contain high levels of this sugar (Crowe and Crowe, 1986, supra).

The results of this study demonstrate that conidia of *T. harzianum* can be produced at high levels in liquid fermentation, and that this conidial biomass is effective in biological control of P. ultimum. However, initial media produced conidia with low levels of viability after drying, and which gave variation when cfu/g were determined. These disadvantages were largely overcome by producing conidia in media with low levels of osmotic potential. Spores produced in such media contained increased levels of trehalose relative to ones produced at high osmotic levels; increased trehalose level has been shown in other organisms to enhance their ability to withstand drying. Conidial biomass with the properties of that produced in the media of low osmotic potential should be very useful in the biological control of plant pathogens.

We claim:

1. A method of increasing the percentage of viable dried spores of a fungus of a genus selected from the group consisting of Trichoderma, Gliocladium, Collectotrichum, and Fusarium, which comprises the steps of:
   (a) inoculating an aqueous growth medium with a suspension of spores of said fungus to provide an inoculated aqueous growth medium,
   (b) culturing said inoculated aqueous growth medium to increase the density of the spores,
   (c) adding a non-toxic osmoticant to said aqueous growth medium before said inoculation or after said inoculation, wherein the osmoticant added to the aqueous growth medium after said inoculation is added before or while the density of the spores is increasing; said osmoticant being added in an amount to provide an osmotic potential to said aqueous medium between about $-1.5$ and $-2.1$ mPa,
   (d) harvesting the spores,
   (e) drying the harvested spores.

2. The method of claim 1 wherein the spores are conidia of Trichoderma.

3. The method of claim 2, wherein step (b) comprises maintaining the inoculated aqueous growth medium under agitation and aeration at a temperature ranging from about 25° C. to about 30° C. and a pH ranging from about 5.8 to about 7.0 to increase the density of the conidia to at least $1 \times 10^8$ conidia per ml.

4. The method of claim 3 wherein the osmoticant is mannitol.

5. The method of claim 3 wherein the osmoticant is inorganic salt.

6. The method of claim 3 wherein the osmoticant is polyalkylene oxide.

7. The method of claim 2 wherein the osmoticant is added after density increase is started, but while density increase is continuing.

8. The method as in claim 3 where the osmoticant is added to the aqueous growth medium before or at about the time of the inoculation of step (a).

9. The method as in claim 3 where the aqueous growth medium is a minimal medium.

10. The method of claim 1 wherein step (c) causes formation of trehalose in the spores and wherein the spores harvested in step (d) are suspended in water prior to step (e).

* * * * *